United States Patent [19]

Honda et al.

[11] Patent Number: 6,010,699

[45] Date of Patent: *Jan. 4, 2000

[54] METHOD FOR CONTROLLING AXIAL LENGTH OF THE EYE

[75] Inventors: Shigeru Honda, Kobe; Noriko Watanabe, Suita; Takahiro Ogawa, Nishinomiya, all of Japan

[73] Assignee: Senju Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/815,941

[22] Filed: Mar. 13, 1997

[30] Foreign Application Priority Data

Mar. 15, 1996 [JP] Japan .................................. 8-087631

[51] Int. Cl.⁷ .......................... A61K 38/49; A61K 38/16
[52] U.S. Cl. ................................. 424/94.63; 424/94.64; 514/2; 514/12
[58] Field of Search ........................ 514/2, 12; 435/215, 435/217; 530/350, 351; 424/94.64, 94.63

[56] References Cited

U.S. PATENT DOCUMENTS 5,652,209  7/1997  Pflugfelder et al. .
5,656,726  8/1997  Rosenberg et al. .
5,688,765  11/1997  Sullivan .

FOREIGN PATENT DOCUMENTS

WO/9405322  3/1994  WIPO .

OTHER PUBLICATIONS

O'Brart et al., *Ophthalmology*, 101(9):1565–74, 1994.
Honda et al., *Invest. Ophthalmol. Vis. Sci.*, 37(12):2519–26, Nov. 1996.
Rohrer et al., *Experimental Eye Research*, 58(5):553–561.

*Primary Examiner*—Marianne P. Allen
*Attorney, Agent, or Firm*—Wenderoth, Lind & Ponack, L.L.P.

[57] ABSTRACT

A method for controlling axial length, comprising administering a pharmaceutically effective amount of a TGF-β regulating substance. More particularly, a method for inhibiting axial elongation and a method for the prophylaxis and treatment of myopia, both comprising administering a TGF-β activator, specifically a plasminogen activator. A method for elongation of axial length and a method for the prophylaxis and treatment of hyperopia, both comprising administering a TGF-β activation inhibitor, particularly a plasminogen activator inhibitor. The method for controlling axial length of the present invention is extremely useful for the prophylaxis and treatment of myopia or hyperopia. It is also useful for preparing experimental model animals having eyes with complete axial myopia or hyperopia exclusive of refractive myopia or hyperopia.

12 Claims, 3 Drawing Sheets

ONL : Outer nuclear layer

PRL : Photoreceptor layer

RPE : Retinal pigment epithelium

CHO : Choroid

SCL : Sclera

METHOD FOR CONTROLLING AXIAL LENGTH OF THE EYE

BACKGROUND OF THE INVENTION

(1) Field of the Invention

The present invention relates to a method for controlling axial length and a method for the prophylaxis and treatment of myopia or hyperopia.

(2) Description of the Related Art

It is a world-wide tendency that patients with myopia, particularly axial myopia, is increasing in number, and when the symptom is severe, it may often induce myopic macular atrophy or retinal detachment which may result in the loss of sight. The axial myopia is a state where the axial length is too long, so that the light from infinite distance forms images before retina. Conversely, a state where the axial length is too short, so that the light from infinite distance forms images behind retina is axial hyperopia. The axial hyperopia is caused by immature growth of eye globes. As the etiology of myopia or hyperopia, there are various theories accusing visual environment during infancy and school age, genetic factor and so on. However, no experimentally-supported elucidation has been heretofore made.

It is therefore an object of the present invention to identify the physiologically active substance responsible for the short or long axial length and provide a method for prophylaxis and treatment of myopia or hyperopia, comprising administering said substance to a patient and a future patient.

SUMMARY OF THE INVENTION

The present inventors first found that the level of TGF-β (transforming growth factor β) was lower in the retina-RPE (retinal pigment epithelium)-choroid of the eyes of models with form-deprivation myopia. Based on this finding, it has now been clarified that the administration of a plasminogen activator (hereinafter sometimes abbreviated as PA) indirectly suppresses axial elongation as a result of an increase in active TGF-β in retina-RPE-choroid, and that the administration of plasminogen activator inhibitor (hereinafter sometimes abbreviated as PAI) conversely elongates axial length. It has been also found that a preparation containing such TGF-β regulating substance as an active ingredient is effective for the phophylaxis and treatment of myopia or hyperopia.

Accordingly, the present invention relates to a method for controlling axial length, comprising administering a pharmaceutically effective amount of a TGF-β regulating substance. More particularly, the present invention relates to a method for inhibiting elongation of axial length, comprising administering a pharmaceutically effective amount of a TGF-β activator, specifically PA, and most specifically urokinase plasminogen activator (hereinafter sometimes abbreviated as uPA), in particular, said method for the prophylaxis and treatment of myopia, and a method for axial elongation comprising administering a TGF-β activation inhibitor, specifically PAI, and most specifically PAI-1 (one of physiological plasminogen activator inhibitors), in particular, said method for the prophylaxis and treatment of hyperopia. The present invention further relates to a method of controlling axial length, comprising administering a TGF-β regulating substance locally to the eye, as well as a method for the prophylaxis and treatment of myopia or hyperopia.

DETAILED DESCRIPTION OF THE INVENTION

Figure 1:
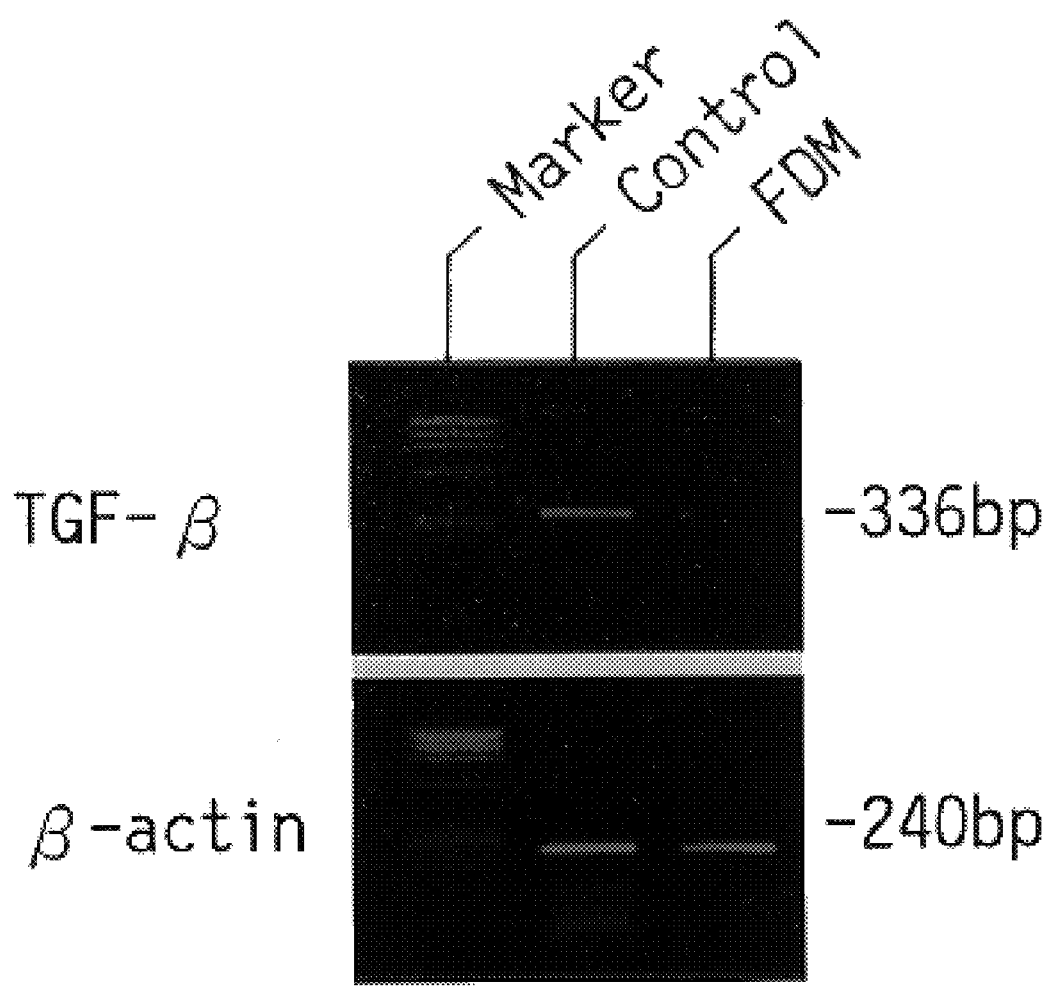
FIG. 1 is an electrophoretic image showing the RT-PCR analysis of TGF-β expressed in retina-RPE-choroid of chick eye having form-deprivation myopia.

A TGF-β is a protein which acts as a growth inhibitor on various cells such as hepatocytes, vascular endothelial cells, hemocytes, lymphocytes and the like, and locally exists in visual cells (cells responsible for photochemical reaction in the most initial stage of visual reception) in the retina. The TGF-β is first synthesized as an inert precursor (latent TGF-β) protein containing a prosequence, after which the prosequence is removed to give an active (mature) TGF-β.

In the present invention, a TGF-β regulating substance means a TGF-β activator which cleaves the prosequence of latent TGF-β to produce active TGF-β, or a TGF-β activation inhibitor which suppresses production of active TGF-β by inhibiting said activator.

The TGF-β activator may itself cleave the prosequence of latent TGF-β or indirectly act thereon. Examples of the former include proteases such as plasmin, cathepsin D, streptokinase, staphylokinase and the like. Examples of the latter include PA, retinoid, phorbol ester, tamoxifen, interleukin-1 and the like which act on TGF-β producing cells. These activators may be naturally occurring or synthetic. The natural ones are not limited in terms of derivation, and may be derived from, for example, mammals such as human, cow, horse, swine, sheep and the like, or birds such as chicken, quail, dove, turkey and the like. Alternatively, they may be derived from microorganisms obtained by genetic recombination, which produce the above-mentioned activators.

The TGF-β activation inhibitor is exemplified by the inhibitors of the above-mentioned TGF-β activators. These inhibitors may be naturally occurring or synthetic. The natural ones are not limited as to their derivation, and may be originated from, for example, mammals such as human, cow, horse, swine, sheep and the like, or birds such as chicken, quail, dove, turkey and the like. Also, they may be derived from microorganisms obtained by genetic recombination, which produce the above-mentioned activation inhibitors.

The TGF-β activator to be used in the present invention is preferably PA. PA includes, but not limited to, vascular plasminogen activator (vPA), tissue plasminogen activator (tPA) and urinary (urokinase) plasminogen activator (uPA). Preferred is uPA. The TGF-β activation inhibitor to be used in the present invention is exemplified by natural PAI, particularly PAI-1.

These substances are biological components having less toxicity, so that they can be administered safely.

The axial length in the present invention means the length of from the anterior pole to posterior fovea of the eye globe. The axial length control agent reduces or elongates the axial length and/or suppresses elongation or decrease of the axial length to maintain the axis at a certain length.

The method for controlling axial length of the present invention comprises administering, to a patient, a pharmaceutically effective amount of a TGF-β activator as an axial elongation inhibitor, or a pharmaceutically effective amount of a TGF-β activation inhibitor as an axial elongation agent. The axial elongation inhibitor means a pharmaceutical preparation for inhibiting elongation of axial length and/or reducing axial length, and the axial elongation agent means a pharmaceutical preparation for elongation of axial length and/or inhibition of reduction of axial length.

The axial elongation inhibitor of the present invention suppresses axial elongation and/or reduces the axial length, so that it can make an agent effective for the prophylaxis and treatment of myopia, particularly axial myopia. The axial elongation agent of the present invention increases the axial length and/or suppresses reduction of axial length, and is effective for the prophylaxis and treatment of hyperopia, particularly axial hyperopia. Hence, the method of the prophylaxis and treatment of myopia or hyperopia of the present invention comprises administering a pharmaceutically effective amount of the above-mentioned axial elongation inhibitor or axial elongation agent to a patient and a future patient.

The agent for the prophylaxis and treatment of myopia or hyperopia of the present inventing is characterized by the control of the activity of endogeneous TGF-β. Hence, it does not affect the locality of the TGF-β in the living body and can be administered safely without causing severe side effects.

The axial length control agent and agent for the prophylaxis and treatment of myopia or hyperopia of the present invention can be produced by mixing the above-mentioned TGF-β regulating substance and a pharmaceutically acceptable carrier. Examples of the pharmaceutically acceptable carrier include excipients (e.g., lactose, corn starch, mannitol, crystalline cellulose and the like), lubricants (e.g., magnesium stearate, talc, polyethylene glycol, colloidal silica and the like), binders (e.g., syrup, gum arabic, gelatin, tragacanth gum, polyvinylpyrrolidone and the like), disintegrators (e.g., potato starch, calcium calboxymethylcellulose, croscarmellose sodium, chitin, chitosan and the like), and the like for solid preparations; and non-aqueous vehicles (e.g., alcohols such as ethanol, propylene glycol and glycerine, oils such as olive oil, almond oil, sesame oil, cotton seed oil, castor oil and corn oil, oil ester and the like), solubilizers (e.g., polyvinylpyrrolidone, cyclodextrin, caffeine, polyethylene glycol and the like), suspending agents (e.g., surfactants such as stearyl triehtanolamine, sodium laurylsulfate and polysorbate 80, hydrophilic polymers such as hydroxyethylcellulose, carboxymethylcellulose, gelatin and sorbit syrup and the like), thickeners (e.g., egg yolk lecithin, gelatin, gum arabic, tragacanth gum, methylcellulose, pectin and the like), isotonizing agents (e.g., sorbitol, glycerol, polyethylene glycol, glucose, sodium chloride and the like), emulsifiers (e.g., lecithin, sorbitan monooleate and the like), buffers (e.g., phosphate buffer, borate buffer, citrate buffer, tartrate buffer, acetate buffer and the like), analgesic agents (e.g., benzyl alcohol and the like), and the like for liquid preparations, which are added as appropriate. Where necessary, preservatives (e.g., p-hydroxybenzoic acid ester, benzalkonium chloride, chlorobutanol and the like), chelating agents (e.g., sodium edetate, sodium citrate, condensed sodium phosphate and the like), antioxidants (e.g., nitrate, ascorbic acid, cysteine and the like), colorants (e.g., tar pigment, glycyrrhiza extract, riboflavin and the like), sweeteners (e.g., glucose, sucrose, saccharin and the like), flavors (e.g., vanillin, menthol and the like), aromatics (e.g., anise oil, menthol and the like), and the like may be added by a conventional method.

Besides those mentioned above, agar, casein, collagen and the like may be added as a pharmaceutically acceptable carrier.

The agent for the prophylaxis and treatment of myopia of the present invention may contain other agent for the prophylaxis and treatment of myopia, such as a pharmaceutical agent containing neostigmine methyl sulfate, tropicamide and the like as an active ingredient, other active ingredients and the like as appropriate. The agent for the prophylaxis and treatment of hyperopia of the present invention may contain other active ingredients and the like as appropriate.

When the axial length control agent of the present invention is used in the form of an aqueous preparation, it preferably has a pH of 4–9 in consideration of stability and physiological activity of TGF-β regulating substance.

As the solid oral preparation, tablets, capsules, granules, powders and the like are exemplified. For example, tablets can be produced by adding the above-mentioned excipients, disintegrators, binders, lubricants and the like to a TGF-β regulating substance as appropriate and compression-forming the resulting mixture. When desired, the above-mentioned sweeteners, flavors, aromatics and the like may be further added after compression forming. For enteric coating and/or for stabilization, a coating agent know per se may be applied, such as synthetic or semi-synthetic substances (e.g., carboxymethylcellulose, hydroxymethylcellulose phthalate and Eudragit), natural substances (i.e., shellac) and mixtures of copolymer of methacrylic acid and ethyl acrylate and copolymer of methacrylic acid and methyl methacrylate.

The oral liquid preparation is exemplified by aqueous or oily suspension, solution, syrup, elixir and the like. For example, a liquid suspension can be produced by suspending a TGF-β regulating substance in the above-mentioned solvent. When desired, the above-mentioned suspending agent may be added as appropriate.

Parenteral preparations include, for example, injection, agent for local administration to the eye and the like.

Injections are exemplified by retrobulbar injection, subcutaneous injection, intravenous injection, intramuscular injection and the like. The injections may be aqueous or non-aqueous, or a solution or suspension.

The preparation for local administration to the eye is exemplified by eye drop, eye ointment, gel and the like, with preference given to eye drop. The eye drop may be aqueous or non-aqueous, or a solution or suspension, with preference given to an aqueous eye drop.

An injection can be prepared by, for example, dissolving a TGF-β regulating substance in sterile purified water for injection together with a preservative (e.g., p-hydroxybenzoic acid ester, benzalkonium chloride, chlorobutanol and the like), an isotonizing agent (e.g., sorbitol, glycerol, polyethylene glycol, glucose, sodium chloride and the like), and the like to give an aqueous injection, or dissolving or suspending in a non-aqueous vehicle (e.g., alcohols such as ethanol, propylene glycol and glycerine, oils such as olive oil, almond oil, sesame oil, cotton seed oil, castor oil and corn oil, oil ester and the like) to give a non-aqueous injection.

An aqueous eye drop can be prepared by, for example, heating purified water, dissolving a pereservative, adding a solubilizer where necessary, and adding a TGF-β regulating substance, followed by complete dissolution of the components. In addition, additives generally used for aqueous eye drops, such as buffers, isotonizing agents, stabilizers (chelating agents), pH adjustors and the like may be concurrently used.

Examples of the preservative include p-hydroxybenzoic acid ester, inverted soaps (e.g., benzalkonium chloride, benzetonium chloride, chlorhexidine gluconate and cetylpyridinium chloride), alcohol derivatives (e.g., chlorobutanol, phenethyl alcohol and benzyl alcohol), organic acids and salts thereof (e.g., sodium dehydroacetate, sorbic acid and salts thereof), phenols (e.g., p-chlormethoxyphenol and p-chlormethacresol), organic mercury compound (e.g., thimerosal, phenylmercuric nitrate and nitormersol), and the like.

The solubilizer is exemplified by polyvinylpyrrolidone, cyclodextrin, caffeine and the like; buffer is exemplified by phosphate, borate, acetate, citrate, amino acid salt and the like; isotonizing agent is exemplified by sodium chloride, sorbitol, mannitol, glycerol, polyethylene glycol, glucose and the like; stabilizer (chelating agent) is exemplified by sodium edetate, sodium citrate, condensed sodium phosphate and the like; and pH adjusting agent is exemplified by hydrochloric acid, acetic acid, methaphosphoric acid, sodium hydroxide and the like.

The aqueous eye drop can be also prepared by appropriately adding a water soluble polymer compound, a surfactant and the like. Examples of the water soluble polymer compound include cellulose derivatives such as alkyl cellulose (e.g., methylcellulose and carboxymethylcellulose), hydroxyalkylcellulose (e.g., hydroxypropylmethylcellulose and hydroxyethylcellulose), vinyl polymer compound (e.g., polyvinylpyrrolidone, polyvinyl alcohol, carboxyvinyl polymer and anhydrous ethylene maleate polymer), polyhydric alcohol compounds (e.g., polyethylene glycol and polypropylene glycol) and the like. Examples of the surfactant include non-ionic surfactants such as polysorbate and polyoxyethylene hydrogenated castor oil, cationic surfactants such as quaternary ammonium salt, anionic surfactants such as alkyl sulfate, amphoteric surfactants such as lecithin, and the like.

An aqueous eye drop suspension can be produced by appropriately adding, besides the above-mentioned additives usable for aqueous eye drops, suspending agents conventionally used. Examples of the suspending agent include methylcellulose, sodium carboxymethylcellulose, carboxy vinyl polymer, hydroxypropylmethylcellulose, polyvinyl alcohol, polyvinylpyrrolidone, polyethylene glycol, sodium chondroitin sulfate, polysorbate 80 and the like.

The above-mentioned aqueous eye drop and aqueous eye drop suspension are preferably adjusted to the pH range conventionally employed for eye drops, which is generally pH 3–8, preferably pH 4–6. For adjusting pH, hydrochloric acid, acetic acid, sodium hydroxide and the like are used.

The above-mentioned aqueous eye drop and aqueous eye drop suspension are preferably adjusted to the osmotic pressure range conventionally employed for eye drops, which is generally 230–450 mOsm, preferably 260–320 mOsm. For adjusting the osmotic pressure, sodium chloride, boric acid, glycerol, mannitol and the like are used.

A non-aqueous eye drop can be prepared by dissolving or suspending a TGF-β regulating substance in a non-aqueous vehicle such as water soluble solvents (e.g., alcohols such as ethanol, propylene glycol and glycerol) and oily solvents (e.g., fats and oils such as olive oil, almond oil, sesame oil, cotton seed oil, castor oil and corn oil and the like).

An eye ointment can be produced by appropriately using, for example, petrolatum, plastibase, liquid paraffin and the like as a base material.

An ophthalmic gel can be produced by appropriately using, for example, carboxyvinyl copolymer, anhydrous ethylene maleate polymer, polyoxyethylene-polyoxypropylene block copolymer, gellan gum and the like as a base material.

The agent for the prophylaxis and treatment of myopia or hyperopia of the present invention is preferably in the dosage form of topical administration to the eye. More preferably, it is in the dosage form of an eye drop, most preferably an aqueous eye drop.

The dosage of the agent for the prophylaxis and treatment of myopia or hyperopia of the present invention need only be in the range of pharmaceutically effective amounts, and varies depending on administration route, severity of the condition, age and body weight of patients, and the like. In the case of PA preparation, for example, it is administered in an amount corresponding to the dose of PA of about 0.1–1000 units/day for an adult where the amount of PA necessary for converting plasminogen under the conditions of 37° C., pH 7.5 to plasmin in an amount sufficient to produce $\Delta A_{275}=1.0$/ml/min of decomposed product of α-casein is defined to be 1 unit. In the case of PAI preparation, the daily dose of PAI for an adult is generally about 0.1–1000 units/day where the amount of PAI capable of inhibiting 1 unit of PA is defined to be 1 unit.

For administration of the agent for the prophylaxis and treatment of myopia or hyperopia of the present invention, an aqueous eye drop containing the active ingredient, TGF-β regulating substance, in an amount of about 1–1000 units/drop, preferably 5–500 units/drop, is instilled to an adult patient with myopia or hyperopia by one to several drops per eye once to several times, preferably twice to five times, a day according to the symptom.

The present invention is described in more detail in the following by way of Formulation Examples as working examples, and the effects of the present invention are clarified by Experimental Examples. It should be noted that these are mere exemplifications and the scope of the present invention is not limited to them.

EXAMPLE 1

Aqueous Eye Drop (1)

Preparation of an aqueous eye drop which is an axial elongation inhibitor (agent for prophylaxis and treatment of myopia) containing uPA as an active ingredient, or an axial elongationagent (agent for prophylaxis and treatment of hyperopia) containing PAI-1 as an active ingredient was prepared.

| Formulation | |
|---|---|
| human-originated μPA lyophilized standard product (or human-originated PAI-1 lyophilized standard product 100,000 units) | 1,000,000 units |
| sodium acetate | 0.5 g |
| benzalkonium chloride | 0.05 g |
| sodium chloride | 6.5 g |
| sodium hydroxide | q.s. |
| dilute hydrochloric acid | q.s. |

Preparation Method

Sterile purified water (800 ml) was heated and benzalkonium chloride was dissolved therein. Then, sodium acetate, sodium chloride, sodium hydroxide and dilute hydrochloric acid were successively added and dissolved. Human-originated uPA or human-originated PAI-1 was added and completely dissolved. This solution was cooled to room temperature and sterile purified water was added to make the total amount 1000 ml. The solution was filtered for sterilization through a 0.22 μm membrane filter and filled in a predetermined container to give an aqueous eye drop.

EXAMPLE 2

Aqueous Eye Drop (2)

Preparation of an aqueous eye drop which is an axial elongation inhibitor (agent for prophylaxis and treatment of myopia) containing uPA as an active ingredient, or an axial elongation agent (agent for prophylaxis and treatment of hyperopia) containing PAI-1 as an active ingredient was prepared.

| Formulation | |
|---|---|
| human-originated μPA lyophilized standard product (or human-originated PAI-1 lyophilized standard product 10,000 units) | 100,000 units |
| boric acid | 16 g |
| sodium tetraborate | 7 g |
| methyl p-hydroxybenzoate | 0.26 g |
| propyl p-hydroxybenzoate | 0.14 g |
| Total with sterile purified water | 1,000 ml (pH 7.5) |

Preparation Method

Sterile purified water (800 ml) was heated and methyl p-oxybenzoate and propyl p-oxybenzoate were dissolved therein. The mixture was cooled to room temperature. Boric acid and sodium tetraborate were successively added and dissolved. Human-originate uPA or human-originated PAI-1 was added and completely dissolved. Sterile purified water was added to make the total amount 1000 ml. The solution was sterilized by filtration through a 0.22 μm membrane filter and filled in a predetermined container to give an aqueous eye drop.

EXAMPLE 3

Aqueous Eye Drop Suspension

Preparation of an aqueous eye drop suspension which is an axial elongation inhibitor (agent for prophylaxis and treatment of myopia) containing uPA as an active ingredient, or an axial elongation agent (agent for prophylaxis and treatment of hyperopia) containing PAI-1 as an active ingredient was prepared.

| Formulation | |
|---|---|
| sterile lyophilized standard product of human-originated μPA (or sterile lyophilized standard product of human-originated PAI-1 500,000 units) | 5,000,000 units |
| sodium dihydrogenphosphate | 50 g |
| sodium chloride | 9 g |
| polysorbate 80 | 20 g |
| chlorobutanol | 3 g |
| sodium hydroxide | q.s. |
| Total with sterile purified water | 1,000 ml (pH 5.0) |

Preparation Method

Sterile purified water (800 ml) was heated an chlorobutanol was dissolved therein. Then, sodium dihydrogenphosphate, sodium chloride and polysorbate 80 were successively added and dissolved. The mixture was cooled to room temperature. The mixture was adjusted to pH 5.0 with sodium hydroxide, and sterile purified water was added to the total amount of 1000 ml. The solution was sterilized by filtration through a 0.22 μm membrane filter. Previously steriled lyophilized standard product of uPA or PAI-1 was uniformly dispersed therein. The suspension was filled in a predetermined container to give an aqueous eye drop suspension.

EXAMPLE 4

Non-aqueous Eye Drop

Preparation of a non-aqueous eye drop which is an axial elongation inhibitor (agent for prophylaxis and treatment of myopia) containing uPA as an active ingredient, or a non-aqueous eye drop (agent for prophylaxis and treatment of hyperopia) containing PAI-1 as an active ingredient was prepared.

| Formulation | |
|---|---|
| sterile lyophilized standard product of human-originated μPA (or sterile lyophilized standard product of human-originated PAI-1 100,000 units) | 1,000,000 units |
| Total with sterilized cotton seed oil | 1,000 ml |

Preparation Method

Previously sterilized lyophilized standard product of uPA or PAI-1 was added to previously sterilized cotton seed oil, and the mixture was filled in a predetermined container to give a non-aqueous eye drop.

EXAMPLE 5

Aqueous Injection

Preparation of an aqueous injection which is an axial elongation inhibitor (agent for prophylaxis and treatment of myopia) containing uPA as an active ingredient, or an axial elongation agent (agent for prophylaxis and treatment of hyperopia) containing PAI-1 as an active ingredient was prepared.

| Formulation | |
|---|---|
| lyophilized standard product of human-originated μPA (or lyophilized standard product of human-originated PAI-1 100,000 units) | 1,000,000 units |
| Total with sterilized physiological saline | 1,000 ml |

Preparation Method

Lyophilized standard product of human-originated uPA or human-originated PAI-1 was added to sterilized physiological saline (1000 ml), and this solution was sterilized by filtration through a 0.22 μm membrane filter. The solution was filled in a predetermined container to give an aqueous injection.

REFERENCE EXAMPLE 1

Variation in TGF-β, PA and PAI-1 expressed in retina-RPE-choroid of chick eyes with form-deprivation myopia The eyelids of the right eyes of chicks (male white leghorn, two days old) were sutured under deep anesthesia to prepare eyes with form-deprivation myopia (hereinafter abbreviated as FDM). The chicks were reared in a rearing box under 12-hour light-12-hour dark cycle for 10 days. After rearing, the chicks were slaughtered and both eyes were enucleated, which were subjected to the following Tests 1–3 wherein the left eyes were used as control.

Test 1

RNA Analysis

The enucleated eye was divided into anterior and posterior halves, and the retina-RPE-choroid was separated from the posterior eye cup. Total RNA was extracted from the tissue with guanidium isothiocyanate solution and purified by centrifugation in cesium chloride gradients. A single-stranded DNA complementary to each of the total RNA (5 μg) was synthesized by MMuLV reverse transcriptase (TOYOBO, Osaka, Japan) using a random hexamer as a primer. The reaction conditions were 5 minutes at 65° C. (annealing), 60 minutes at 37° C. (transcription ) and 5 minutes at 75° C. (inactivation of RTase). The reaction mixture was subjected to polymerase chain reaction. A set of synthetic oligoprimers [sense primer: 5'-GCCCTGGATACCAACTACTGC-3' (SEQ ID NO: 1); antisense primer: 5'-GCTGCACTTGCAGGAACGCCA-3' (SEQ ID NO: 2) was prepared to amplify TGF-β cDNA. The primers, dNTPs and rTth DNA polymerase were added to the cDNA solution and PCR was performed for 35 cycles of amplification (94° C. for 1 minute, 60° C. for 1 minute and 72° C. for 1.5 minutes), followed by final extension at 72° C. for 10 minutes. The PCR products were separated by 1.5% agarose gel electrophoresis and detected by ethidium bromide staining. Variation in the quantity of RNA subjected to RT-PCR was controlled by monitoring the expression of mRNA that corresponds to β-actin, a house-keeping gene not affected by FDM treatment.

The results are shown in FIG. 1. Equal amounts of the amplified products derived from β-actin cDNA were detectable in the control and FDM eyes, but the intensity of the band corresponding to the amplified products derived from TGF-β cDNA in FDM eye was markedly lower than that in control eye.

Test 2

Immunohistochemical Analysis in FDM Retina

The enucleated eye was fixed for 24 hours in 4% paraformaldelhyde containing 0.2% picric acid. After washing with 30% sucrose in 0.1 M phosphate buffer, the eye was frozen and cut into sections (10 μm in thickness) on a cryostat. The frozen sections were incubated for 20 minutes in phosphate buffered saline (PBS) containing 5% normal goat serum and 0.03% Triton X-100, then reacted with anti-TGF-β antibody (1:1000) at 4° C. for 24 hours in PBS containing 3% normal goat serum and 0.03% Triton X-100. After washing with PBS, the sections were incubated at 4° C. for 2 hours in 50-fold diluted FITC-labeled goat anti-rabbit IgG antibody, after which they were observed with a fluorescent light microscope.

Figure 2:
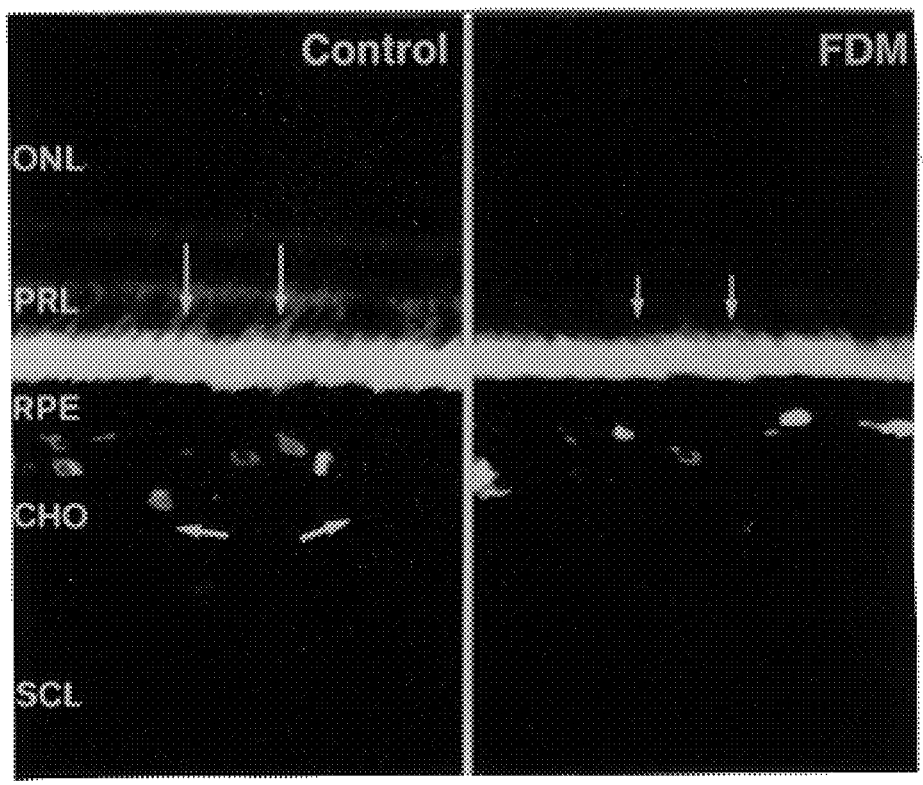
FIG. 2 is a fluorescence microscopic photograph showing immuno-histochemical analysis of TGF-β expressed in a frozen section of chick eye globe having form-deprivation myopia.

The results are shown in FIG. 2. The immunoreactivity with anti-TGF-β antibody was mainly detected throughout the photoreceptor layer in the retina. The immunoreactivity in the FDM eye was less as compared with that in the control eye (FIG. 2, arrows).

Test 3

Immunoblot Analysis

Figure 3:
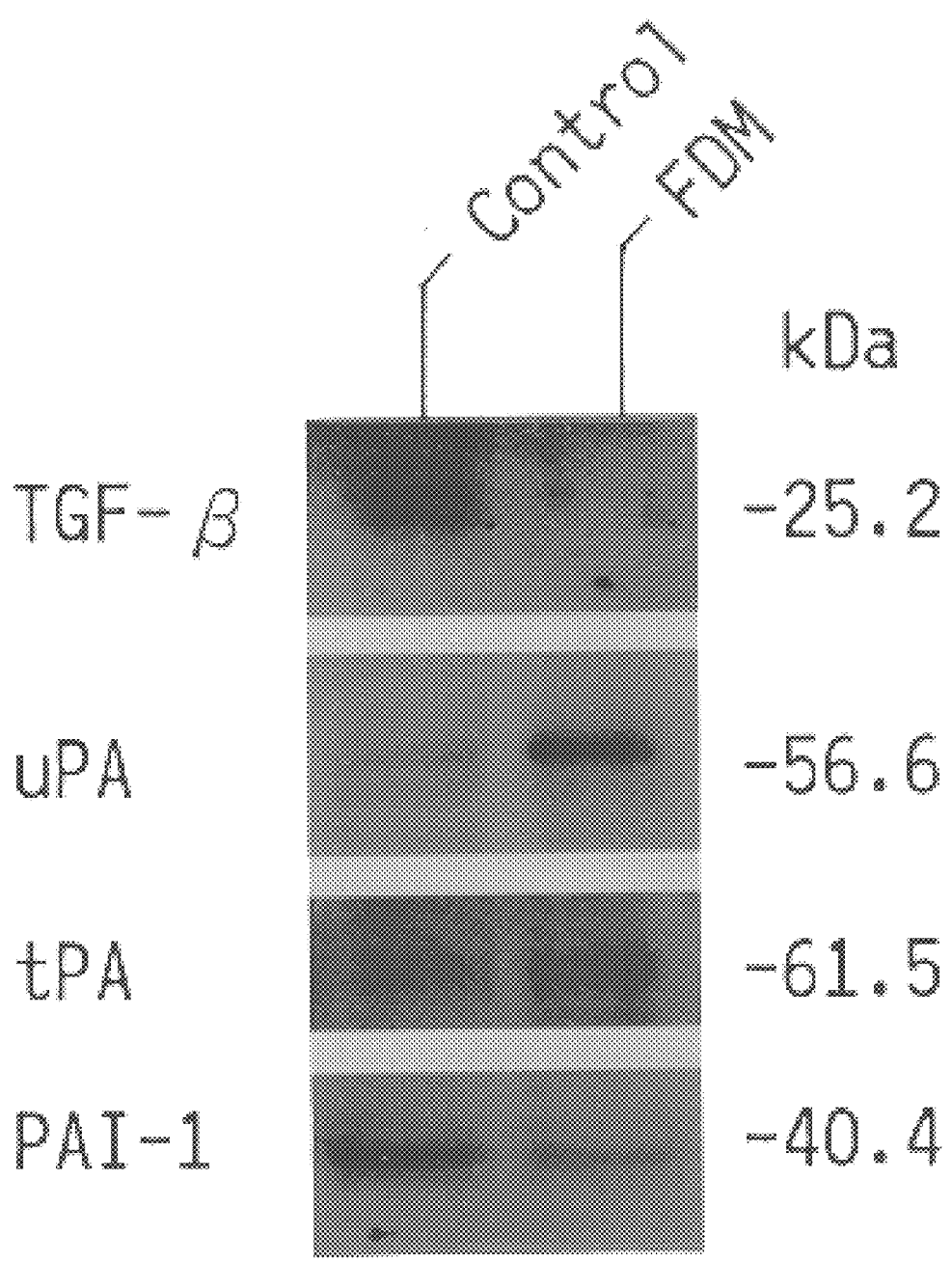
FIG. 3 is an electrophoretic image showing the immunoblot analysis of TGF-β, uPA, tPA and PAI-1 expressed in retina-RPE-choroid of chick eye having form-deprivation myopia.

The retina-RPE-choroid sample was prepared as described in Test 1. The sample was washed with PBS, ice-cooled and homogenized with an extraction buffer [100 mM Tris-HCl (pH 7.4), 100 mM ethylenediaminetetraacetic acid (EDTA), 0.5 mM phenylmethylsulfonyl fluoride (PMSF) and 20 μM leupeptin]. The homogenate was centrifuged at 1,000×g for 20 minutes and the supernatant was recovered. The protein concentration was determined by the Lowry method and the protein concentration of each sample was equalized with the extraction buffer. A sample buffer containing 5% SDS and 10% 2-mercaptoethanol was added and the mixture (protein amount 20 μg) was subjected to SDS-polyacrylamide gel electrophoresis [15% gel for TGF-β, 7.5% gels for uPA, tPA and PAI-1]. After migration, each gel was electrotransferred to a PVDF filter (Millipore, Mass. U.S.A.) using a transfer device, washed and blocked (10% gelatin for 12 hours). Using rabbit anti-TGF-β, anti-uPA, anti-tPA and anti-PAI-1 polyclonal antibody as a primary antibody, and peroxidase-labeled goat anti-rabbit IgG as a secondary antibody, antigen-antibody reaction was performed. The filter was washed with PBS, and allowed to develop color using an enhanced chemiluminescence detection kit (Renaissance, Du Pont.NEN, Massachusetts, U.S.A.) to confirm expression of TGF-β, uPA, tPA and PAI-1. The results are shown in FIG. 3. In FDM, the band of TGF-β disappeared and expression of uPA was found. The expression of PAI-1 was less than that in the control eye. As regards tPA, no significant difference was found between FDM and the control eye.

From the foregoing results, it was postulated that PA and PAI-nondependent decrease of TGF-β occurred in the retina-RPE-choroid tissue of FDM; uPA which did not express in normal eye, expressed as a repairing mechanism and PAI-1 which is the inhibitor thereof decreased.

EXPERIMENTAL EXAMPLE 1

Reduction of axial length by the administration of aqueous injection containing uPA, and axial elongation by the administration of aqueous injection containing PAI-1

Fifteen chicks (male white leghorn, two days old) were divided into 3 groups (uPA group, PAI group, physiological saline group, 5 chicks each), and an aqueous injection containing uPA prepared in Example 5 was administered to uPA group in both eyes; an aqueous injection containing PAI-1 prepared in Example 5 was administered to PAI group in both eyes; and physiological saline was administered to physiological saline group by retrobulbar injection by 50 μl once a day for 10 days, during which period the chicks were reared in rearing box under 12-hour light-12-hour dark cycle. After rearing, anterior chamber depth (ACD), lens thickness (LT), vitreous chamber depth (VCD) and axial length (AL) were measured using an ultrasonic determination device under deep anesthesia.

As a result, the uPA group showed smaller VCD and AL than those of the physiological saline group. Conversely, the PAI group showed greater VCD and AL than those of the physiological saline group. With regard to ACD and LT, the groups administered with the test drug did not show significant difference from the physiological saline group (Table 1). The results demonstrated that uPA caused reduction of axial length in the normal eye, particularly that due to structural changes in retina, choroid, sclera and the like. On the other hand, PAI-1 evidently caused axial elongation in the normal eye, particularly that due to structural changes in retina, choroid, sclera and the like.

TABLE 1

Effect of TGF-β regulating substance on axial length and the length of axis-constituting portions of nondeprived eye

| groups | ACD | LT | VCD | AL (mm) |
|---|---|---|---|---|
| P-S group | 1.454 ± 0.027 | 2.513 ± 0.092 | 5.123 ± 0.098 | 9.090 ± 0.091 [1] |
| μPA group | 1.427 ± 0.046 | 2.539 ± 0.069 | 5.036 ± 0.038 [2] | 9.001 ± 0.055 [2] |
| PAI group | 1.432 ± 0.038 | 2.544 ± 0.036 | 5.221 ± 0.103 [2] | 9.197 ± 0.109 [2] |

P-S group: group administered with physiological saline
[1] mean ± standard deviation (n = 10)
[2] $p < 0.05$

EXPERIMENTAL EXAMPLE 2

Prophylaxis and treatment of myopia by the administration of aqeuous injection containing uPA The eyelids of the right eyes of fifteen chicks (male white leghorn, two days old) were sutured under deep anesthesia to prepare FDM. The chicks were divided into 3 groups (uPA group, PAI group, physiological saline group, 5 chicks each), and each drug was administered to the sutured eyes in the same manner as in Experimental Example 1. Physiological saline was administered to the non-sutured eyes (left eye) and used as control. At the end of rearing, anterior chamber depth (ACD), lens thickness (LT), vitreous chamber depth (VCD) and axial length (AL) were measured using an ultrasonic determination device under deep anesthesia. The results are shown in Table 2.

The sutured eye of the physiological saline group showed smaller ACD and greater LT, VCD and AL as compared to the measures of the control group. In particular, VCD and AL showed noticeable increases. Since FDM is mainly caused by axial elongation induced by structural changes in retina, choroid, sclera and the like, the results coincided well with the characteristics of FDM.

The uPA group showed smaller VCD and AL than those of the physiological saline group and showed almost the same measures with the control eye. With regard to ACD and LT, no significant results were obtained as compared to the physiological saline group. These results established that the administration of uPA suppressed axial elongation, particularly that due to structural changes in retina, choroid, sclera and the like. That is, uPA is effective for the prophylaxis and treatment of myopia.

On the other hand, the PAI group did not show any significant difference from the physiological saline group in ACD, LT, VCD or AL, which suggested that PAI-1 did not directly control axial elongation.

TABLE 2

Effect of TGF-β regulating substance on axial length and the length of axis-constituting portions of nondeprived eye

| groups | ACD | LT | VCD | AL (mm) |
|---|---|---|---|---|
| P-S group | 1.204 ± 0.068 | 2.564 ± 0.024 | 5.535 ± 0.164 | 9.303 ± 0.192 [1] |
| μPA group | 1.127 ± 0.079 | 2.579 ± 0.054 | 5.241 ± 0.199 [2] | 8.963 ± 0.178 [2] |
| PAI group | 1.177 ± 0.078 | 2.622 ± 0.045 | 5.466 ± 0.397 | 9.263 ± 0.387 |

P-S group: group administered with physioligical saline
[1] mean ± standard deviation (n = 5)
[2] $p < 0.05$ The results of Experimental Examples 1 and 2 and Reference Example 1 strongly indicate that uPA and PAI-1 indirectly controlled axial length by regulating activation of TGF-β. In other words, uPA activates latent TGF-β in retina-RPE-choroid and produced TGF-β acts as a growth inhibitor to reduce axial length (suppression of axial elongation). On the other hand, PAI-1 inhibits activation of latent TGF-β in retina-RPE-choroid, by which it elongates axial length (suppression of reduction of axial length).

In Experimental Example 2, the administration of PAI-1 did not cause axial elongation. This may be explained that TGF-β, which is to be inhibited by PAI-1, was so low in FDM that the effect of PAI-1 was not distinct. It is considered that, when uPA was administered, positive self-induction by the activation of TGF-β occurred and TGF-β was newly biosynthesized.

The method for controlling axial length of the present invention corrects axial length and suppresses abnormal elongation or reduction of the axial length. Therefore, it is extremely useful for the prophylaxis and treatment of myopia or hyperopia. The method for controlling axial length of the present invention reduces or elongates only vitreous chamber depth and does not change anterior chamber depth or lens thickness, so that it is markedly useful for preparing experimental model animals having eyes with complete axial myopia or hyperopia exclusive of refractive myopia or hyperopia.

This application is based on application No. 87631/1996 filed in Japan, the content of which is incorporated hereinto by reference.

What is claimed is:

1. A method for inhibiting axial elongation, comprising administering to a patient or animal a pharmaceutically effective amount of a plasminogen activator to inhibit axial elongation.

2. The method of claim 1, wherein the plasminogen activator is a urokinase.

3. The method of claim 2, wherein the urokinase is locally administered to an eye of the patient or animal.

4. The method of claim 1, wherein the plasminogen activator is locally administered to an eye of the patient or animal.

5. The method of claim 1, wherein the patient is myopic.

6. The method of claim 5, wherein the plasminogen activator is a urokinase.

7. The method of claim 6, wherein the urokinase is locally administered to an eye of the patient or animal.

8. The method of claim 5, wherein the plasminogen activator is locally administered to an eye of the patient or animal.

9. A method for promoting axial elongation, comprising administering to a patient or animal a pharmaceutically effective amount of a plasminogen activator inhibitor to promote axial elongation.

10. The method of claim 9, wherein the plasminogen activator inhibitor is locally administered to an eye of the patient or animal.

11. The method of claim 9, wherein the patient is hyperopic.

12. The method of claim 11, wherein the plasminogen activator inhibitor is locally administered to the eye.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:

-continued (A) LENGTH: 21 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 1:

GCCCTGGATA CCAACTACTG C                                         21

(2) INFORMATION FOR SEQ ID NO: 2:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 2:

GCTGCACTTG CAGGAACGCC AC                                        22